US005549806A

United States Patent [19]

Chen

[11] Patent Number: 5,549,806
[45] Date of Patent: Aug. 27, 1996

[54] DEVICE AND METHOD OF DIRECT WATER COOLING FOR HORIZONTAL SUBMARINE GEL ELECTROPHORESIS

[76] Inventor: Stephen L. Chen, 13800 SW. 185th Ave., Aloha, Oreg. 97006

[21] Appl. No.: 603,625

[22] Filed: Feb. 21, 1996

[51] Int. Cl.$^6$ .................. G01N 27/26; G01N 27/447
[52] U.S. Cl. .................. 204/621; 204/456; 204/466; 204/606; 204/616
[58] Field of Search .................. 204/621, 456, 204/457, 458, 459, 461, 462, 463, 464, 465, 466, 467, 468, 469, 470, 606, 607, 608, 609, 610, 612, 613, 614, 615, 616, 617, 618, 619, 620

[56] References Cited

U.S. PATENT DOCUMENTS

| | | | |
|---|---|---|---|
| 3,047,489 | 7/1962 | Raymond | 204/616 |
| 3,371,027 | 2/1968 | La Paglia et al. | 204/618 |
| 3,407,133 | 10/1968 | Oliva et al. | 204/616 |
| 3,432,414 | 3/1969 | Rand | 204/461 |
| 3,563,880 | 2/1971 | Anderson | 204/621 X |
| 3,578,604 | 5/1971 | Uriel | 204/470 X |
| 3,677,930 | 7/1972 | Mesbane et al. | 204/607 |
| 3,930,973 | 1/1976 | Nerenberg | 204/466 X |
| 3,947,345 | 3/1976 | Grandine et al. | 204/621 X |
| 4,151,065 | 4/1979 | Kaplan et al. | 204/621 |
| 4,190,517 | 2/1980 | Monthony et al. | 204/621 |
| 4,588,491 | 5/1986 | Kreisher et al. | 204/621 X |
| 4,624,768 | 11/1986 | Yoshida et al. | 204/621 X |
| 4,702,814 | 10/1987 | Audeh | 204/616 |
| 4,814,057 | 3/1989 | Nishizawa | 204/621 X |
| 5,074,981 | 12/1991 | Fairfield | 204/466 |
| 5,137,613 | 8/1992 | Brumley Jr. et al. | 204/621 |

OTHER PUBLICATIONS

Products Catalog (1994) of Hoefer Scientific Instruments p. 30 654 Minnesota St. Box 77387 San Francisco, CA 94107.

*Primary Examiner*—Kathryn Gorgos
*Assistant Examiner*—John S. Starsiak, Jr.

[57] ABSTRACT

A device and method of direct water cooling for horizontal submarine gel electrophoresis is provided. A cooling water is utilized to replace a buffer for immersing a gel matrix during electrophoresis. The replacement offers an excellent heat absorption and a substantial reduction of electric current simultaneously, which enables the horizontal submarine gel electrophoresis to be performed at elevated voltages.

6 Claims, 1 Drawing Sheet

DEVICE AND METHOD OF DIRECT WATER COOLING FOR HORIZONTAL SUBMARINE GEL ELECTROPHORESIS

BACKGROUND OF THE INVENTION

1. Field of the Invention

The present invention relates to devices and methods in horizontal submarine gel electrophoresis. In particular, the present invention relates to devices and methods for decreasing temperature in gel matrix so that higher voltage can be applied to the gel matrix in horizontal submarine gel electrophoresis.

2. Background of the Invention

Gel electrophoresis is one of the most commonly utilized tools in biomedical researches and industries. In gel electrophoresis, a sample mixture of biomolecules is applied to a gel matrix and an electric field is also applied to the gel matrix via a buffer system. The charged components in the sample mixture migrate through the gel matrix at different migration rates so that they can be separated from each other after electrophoresis. The migration rate of the charged components is directly related to the voltage of the electric field applied. Higher voltage generates higher migration rate under a given condition.

Gel matrixes used in electrophoresis are made from their gel solutions via different mechanisms. Polyacrylamid gel matrix is formed from a gel solution by a chemical reaction. Agarose gel matrix, in contrast, is formed from a gel solution by a decrease in temperature. The from agarose gel matrix is readily reversible whenever the temperature rises to a certain point. The properties of the agarose gel matrix are significantly altered by a temperature elevation due to the nature of the gel forming mechanism. Thus, it is critical for agarose gel electrophoresis to maintain the gel matrix at a low temperature.

Conventional horizontal submarine gel electrophoresis is the most commonly used format for agarose gel due to its simplicity in gel formation and manipulation. The gel matrix is usually casted in an open tray and the tray with the gel is then immersed into a buffer system for applying an electric field to the gel matrix and absorbing heat from the gel matrix. A typical feature of this format is that a heavy electric current passes through two pathways, a gel pathway through the gel matrix and a buffer pathway through the buffer around the gel matrix. The heavy electric current causes a massive heat generation during electrophoresis.

Gel pathway and buffer pathway are two partners in forming electric circuit. The condition of the buffer pathway around the gel matrix affects the result of the electrophoresis in the gel matrix due to their partnership relation. Thus, the consistency of electrophoresis can be ruined by buffer related manual variations. Such as the volume of the buffer used, the level of the buffer surface adjusted, and the relative ionic strength between the buffer and the gel matrix.

The heavy electric current causes the massive heat generation during electrophoresis. The massive heat must be removed from the gel matrix in order to reduce the temperature of the gel matrix. But, unfortunately, a logic paradox makes the temperature reduction a difficulty in conventional horizontal submarine gel electrophoresis, that is, the temperature of the gel matrix will be further reduced if more buffer is used to cover the gel matrix and the temperature of the gel matrix will be further elevated if more buffer is used to cover the gel matrix. It is a fact that more buffer can absorb more heat from the gel matrix. It is also a fact that more butter will lead to a heavier electric current.

The existence of the buffer pathway around the gel matrix results in disadvantages:

(1) The electrophoresis has to be a slow process because the voltage applied must be limited to a low scale level to avoid generating excess heat which will otherwise distort the gel matrix.

(2) A strong buffering capacity is required for the buffer system to maintain a pH balance under the heavy electric current.

(3) A careful manipulation of adjusting buffer condition is required for reducing the variation of electrophoresis.

These disadvantages are long-problems. Attempts have been made for pursuing improvement of the conventional horizontal submarine gel electrophoresis.

Audeh. U.S. Pat. No. 4,702,814, teaches a horizontal submarine gel device having a gas collecting means and a conduit for eliminating the requirement of having a strong buffering capacity in buffer system. But Audeh fails to recognize the basis of those disadvantages. A buffer pathway is inherited in his device. Thus, Audeh fails to accelerate the slow process of electrophoresis and fails to omit the requirement of adjusting the buffer condition.

Hoefer, 1994 Catalog of Hoefer Scientific Instruments at page 30, teaches a horizontal submarine gel device having a coolant mixture in base chamber for accelerating the slow process of electrophoresis. Hoefer, however, also fails to recognize the basis of those disadvantages. The buffer pathway is still inherited in his device. Hence, Hoefer fail to omit the requirement of adjusting the buffer condition and fails to eliminate the requirement of having strong buffering capacity for maintaining pH balance. Furthermore, Hoefer fails to optimize the acceleration of the slow process of electrophoresis. First, a massive heat is still generating from the buffer pathway around the gel matrix. Secondly, the heat absorption is dramatically barricaded by placing a plastic layer of gel tray and a plastic layer of base chamber between the gel matrix and the coolant. The acceleration is therefore a limited improvement.

Fairfield, U.S. Pat. No. 5,074,981, teaches a device and method for high speed gel electrophoresis. Fairfield has recognized the basis of those disadvantages so that the buffer pathway is removed from his device and method. Bin, Fairfield fails to find a correct solution for most routine applications. To reach his high speed, Fairfield sacrifices the most attractive advantage of conventional horizontal submarine gel electrophoresis, the simplicity, and replaces it with a series of delicate requirements. Such as a series of additional devices, a series of difficulties in manipulation, a series of time-consuming steps, and a series of risks of failure. For example, Fairfield requires a vacuum grease, an external pump, an ice bag, and a thermometer. Fairfield has to deal with difficulties of handling a thin agarose gel, of assembling ice bag over the thin agarose gel without disturbing applied sample, and of controlling all samples into a volume less than 4 μl. Fairfield needs time to prepare all his samples to high concentration in order to load enough amount of sample in a volume less than 4 μl, to cover the gel tightly with plastic wrap, to place gel in 4° C. for at least 30 minutes, and to assemble all required devices together carefully. Fairfield may easily fail by a series of uncertainties, such as the failure in ice crystals penetrating into the gel at −20° C., the failure in making an essential excellent thermal contact at all layers, and the failure in disturbing applied sample during layer assembly.

Fairfield accelerates the slow process of electrophoresis by paying a tremendous price. Such overweight price is constructed as a limiting barrier of its acceptability for most routine applications. Besides, the acceleration does not save time for the whole procedure because Fairfield has to spend a long time to perform his device and method. Fairfield also fails to improve the consistency of electrophoresis because much more manual uncertainties have been introduced in his device and method.

A horizontal submarine gel electrophoresis device and method with its original simplicity but without those disadvantages is highly desirable but the long-felt problem remains unsolved.

It is, thereafter, an object of the present invention to remove the basis of those disadvantages, the buffer pathway, while maintaining its original simplicity so that a simple device and method for most routine applications can be provided.

SUMMARY OF THE INVENTION

The present invention provides a device and method of direct water cooling for horizontal submarine gel electrophoresis. A cooling water is used to replace a buffer for immersing the gel matrix. This replacement offers an excellent heat absorption and a substantial reduction of electric current simultaneously, which brings advantages with the present invention.

(1) The original simplicity of conventional horizontal submarine gel electrophoresis is maintained and further advanced.

(2) The whole procedure is accelerated by applying high voltage for electrophoresis and by shortening manipulation.

(3) The requirement of strong buffering capacity for maintaining pH balance is eliminated by removing the buffer pathway.

(4) The requirement of adjusting buffer condition for consistency of electrophoresis is omitted when the buffer pathway is removed.

DETAIL DESCRIPTION OF THE INVENTION

Figure 1:
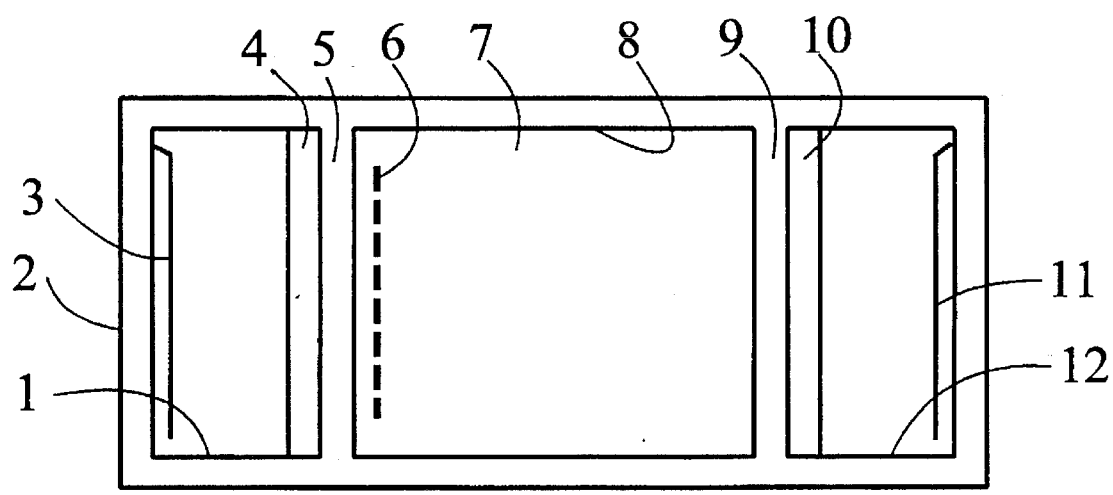
FIG. 1 is a top-side view of a device of the present invention.

FIG. 1 is a top-side view of a device of the present invention.

Figure 2:
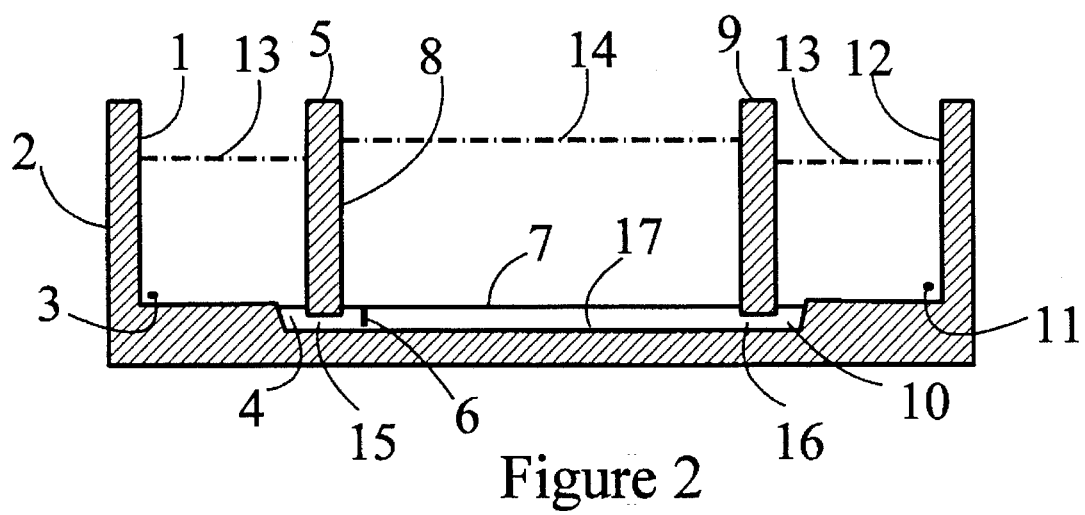
FIG. 2 is a cross-sectional view of the device of the present invention.

FIG. 2 is a cross-sectional view of the device of the present invention.

In a horizontal submarine gel apparatus 2, an interior space is divided into a first buffer chamber 1, a second buffer chamber 12, and a cooling water chamber 8 by a first wall 5 and a second wall 9. A first slot 15 is constructed on first wall 5 at bottom edge and a second slot 16 is constructed on second wall 9 at bottom edge. A gel bed 17 is constructed at bottom of cooling water chamber 8, expanding into both first buffer chamber 1 and second buffer chamber 12 via slot 15 and slot 16 respectively. The top side of both slot 15 and slot 16 is constructed to a level which is 3 mm lower than the level of the top surface of gel matrix 7 so that both first slot 15 and second slot 16 can be sealed by gel matrix 7. Gel matrix 7 has a first end 4 exposing to first buffer chamber 1 via first slot 15 and a second end 10 exposing to second buffer chamber 12 via second slot 16.

An operation procedure of the device and method is as follows:

(1) introducing a gel solution to gel bed 17 to from gel matrix 7 with sample well 6, (2) applying sample to sample well 6, (3) introducing buffer 13 into both first buffer chamber 1 and second buffer chamber 12, (4) introducing cooling water 14 into cooling water chamber 8, and (5) applying an electric field to buffer 13 at an elevated voltage for electrophoresis via first electrode 3 and second electrode 11.

The mechanism of the device and method is as follows:

The buffer in prior arts exhibits two paradoxical effects on the gel matrix. The first one is a heat absorption from the gel matrix to reduce the temperature of the gel matrix. The second one is a massive heat generation from buffer around the gel matrix, which elevates the temperature of the gel matrix.

In the present invention, the two effects of the buffer are separated. The first effect, the heat absorption, is dramatically improved by placing cooling water 14 in large volume directly on top of gel matrix 7. The second effect, the massive heat generation, is eliminated by immersing gel matrix 7 in cooling water 14 rather than in a buffer. It indicates that the temperature of gel matrix 7 can be easily repressed to a low level so that it is now feasible to use higher voltage for accelerating the slow process of electrophoresis.

Cooling water 14 is a distilled water, one of the basic inexpensive supplies in laboratories. Unlike buffers, the distilled water has a high electric resistivity, that is, a low electric conductivity. This property enables cooling water 14 to function as a liquid electric insulator to prevent heavy electric current. The high electric resistivity is well maintained during electrophoresis because all kinds of charged components in gel matrix 7 are driven to move along gel matrix 7 by the powerful electric field applied. Any charged component, if escaping from gel matrix 7 to cooling water 14 via a slow process of diffusion between their interface, will be driven back to gel matrix 7 rapidly by the difference of electric potential.

The consistency of electrophoresis is improved in the present invention. The electric circuit, which is composed of a gel matrix and a butter pathway in prior arts, is now composed of gel matrix 7 only. Manual variations are minimized.

The requirement of a buffer with strong buffering capacity is eliminated in the present invention. The amperage, which is the sum of the electric current from a gel matrix and a buffer pathway in prior arts, is now substantially reduced. The time length needed for electrophoresis is shorten. Hence, a sufficient buffering capacity can be provided by buffer 13 at a greatly reduced volume.

Gel matrix 7 seals first slot 15 and second slot 16 to from liquid barriers. When casting gel matrix 7, The gel solution in gel bed 17 flows into both first slot 15 and second slot 16 automatically. Sample well 6 is constructed in gel matrix 7 in cooling water chamber 8. After a decrease in temperature, the gel solution forms gel matrix 7 which seals both first slot 15 and second slot 16 as liquid impermeable barriers. The difference between the gravity of buffer 13 and the gravity of cooling water 14 is such a negligible force so that gel matrix 7 is capable of sealing the two slots securely. First slot 15 and second slot 16, after being sealed, are still severing as open channels for electric current passing through gel matrix 7. First end 4 and second end 10 of gel matrix 7, however, can be easily cut off when removing gel matrix 7 from cooling water chamber 8 after electrophoresis.

Although the description above contains specifications, it will apparent to those skilled in the art that a number of other variations and modifications may be made in this invention without departing from its spirit and scope. Wall 5 and wall 9, for example, can be constructed as two removable walls, cooling water chamber 8 can be constructed as a removable chamber, cooling water 14 can be further introduced into the space under gel matrix 7, and gel bed 17 can be constructed as a removable part as well. Thus, the description as set out above should not be constructed as limiting the scope of the invention but as merely providing illustration of one of the presently preferred embodiment of the invention.

What is claimed is:

1. A device for direct water cooling for horizontal submarine gel electrophoresis, comprising:

a first slot being constructed between a first buffer chamber and a cooling water chamber, being constructed adjacent to a first end of a gel bed, and being constructed at a level lower than a level of a top surface of a gel matrix, a second slot being constructed between a second buffer chamber and said cooling water chamber, being constructed adjacent to a second end of said gel bed, and being constructed at a level lower than said level of said top surface of said gel matrix, a main body of said gel matrix located in said cooling water chamber, a first end of said gel matrix exposed to said first buffer chamber via said first slot, a second end of said gel matrix exposed to said second buffer chamber via said second slot, and cooling water having direct contact with said main body of said gel matrix in said cooling water chamber.

2. The device of direct water cooling of claim 1 wherein said cooling water chamber is located between said first buffer chamber and said second buffer chamber.

3. The device of direct water cooling of claim 1 wherein said cooling water is a distilled water.

4. A method for direct water cooling in horizontal submarine gel electrophoresis, comprising:

(a) providing a device of direct water cooling for horizontal submarine gel electrophoresis, having:

a first slot being constructed between a first buffer chamber and a cooling water chamber, being constructed adjacent to a first end of a gel bed, and being constructed at a level lower than a level of a top surface of a gel matrix, a second slot being constructed between a second buffer chamber and said cooling water chamber, being constructed adjacent to a second end of said gel bed, and being constructed at a level lower than said level of said top surface of said gel matrix, a main body of said gel matrix located in said cooling water chamber, a first end of said gel matrix exposed to said first buffer chamber via said first slot, a second end of said gel matrix exposing to said second buffer chamber via said second slot, and cooling water having direct contact with said main body of said gel matrix in said cooling water chamber, (b) sealing said first slot and said second slot by forming said gel matrix, and (c) introducing said cooling water into said cooling water chamber in direct contact with said main body of said gel matrix for absorbing heat from said gel matrix.

5. The method of direct water cooling of claim 4 wherein said gel matrix is an agarose gel matrix.

6. The method of direct water cooling of claim 4 wherein said cooling water is a distilled water.

* * * * *